(12) United States Patent
Moerner et al.

(10) Patent No.: US 9,075,010 B2
(45) Date of Patent: Jul. 7, 2015

(54) ENHANCEMENT OF MOLECULAR EMISSION USING OPTICAL-ANTENNA STRUCTURES

(75) Inventors: William E. Moerner, Stanford, CA (US); Anika Kinkhabwala, Stanford, CA (US)

(73) Assignee: The Board of Trustees of the Leland Stanford Junior Univerity, Palo Alto, CA (US)

( * ) Notice: Subject to any disclaimer, the term of this patent is extended or adjusted under 35 U.S.C. 154(b) by 197 days.

(21) Appl. No.: 13/274,915

(22) Filed: Oct. 17, 2011

(65) Prior Publication Data
US 2012/0091365 A1 Apr. 19, 2012

Related U.S. Application Data

(60) Provisional application No. 61/393,709, filed on Oct. 15, 2010.

(51) Int. Cl.
G01N 21/64 (2006.01)
B82Y 15/00 (2011.01)
B82Y 20/00 (2011.01)

(52) U.S. Cl.
CPC .................. *G01N 21/64* (2013.01); *B82Y 15/00* (2013.01); *B82Y 20/00* (2013.01)

(58) Field of Classification Search
CPC ....................................................... G01N 21/64
USPC ............... 250/458.1; 356/301, 317, 445, 504
See application file for complete search history.

(56) References Cited

U.S. PATENT DOCUMENTS

| 7,068,698 B2 | 6/2006 | Moerner et al. |
| 2008/0066549 A1 | 3/2008 | Oldham |

OTHER PUBLICATIONS

Kinkhabwala et al., "Large Single-Molecule Fluorescence Enhancements Produced by a Bowtie Nanoantenna," Nature Photonic (3), Nov. 2009, p. 654-657. (published online Oct. 18, 2009).*
Aouani et al. "Crucial Role of the Adhesion Layer on the Plasmonic Fluorescence Enhancement." ACS Nano, 2009, 3 (7), pp. 2043-2048.*
Jaio et al. (2008), "Localization of Near-Field Resonances in Bowtie Antennae: Influence of Adhesion Layers," Plasmonics (2009) 4, p. 37-50.*
Wang et al. (2007), "High Transmission Bowtie-Shaped Aperture Probe for Near-Field Optical Imaging," Applied Physics Letter (90) 261105, p. 1-3.*
Tam et al. (2007), "Plasmonic Enhancement of Molecular Fluorescence," Nano Letters (7) 2, p. 496-501.*
Wenger et al. (2005), "Single Molecule Fluorescence in Rectangular Nano-Apertures," Optics Express (13) 18, p. 7035-7044.*
Estrada et al. "10000 times volume reduction for fluorescence correlation spectroscopy using nano-antennas." Optics Express 16(25), p. 20597-20602 (Nov. 26, 2008).

(Continued)

*Primary Examiner* — Casey Bryant
(74) *Attorney, Agent, or Firm* — Crawford Maunu PLLC

(57) ABSTRACT

The present disclosure relates to an apparatus, and methods of use, for enhancement of molecular emission by nano-antennas. Using the nano-antennas, the life-time is greatly shortened or the strength of broadly peaking spectral emission of fluorescent molecules is greatly enhanced by a generated electric field. The electric field generated is due to opposing charges located at two metallic end portions of the nano-antenna in response to receiving optical energy.

31 Claims, 8 Drawing Sheets

(56) References Cited

OTHER PUBLICATIONS

Farahani et al., "Bow-tie optical antenna probes for single-emitter scanning near-field optical microscopy." Nanotechnology 18, p. 1-4 (Feb. 23, 2007).
Anger et al., "Enhancement and Quenching of Single-Molecule Fluorescence." Phys. Review Letters 96, p. 113002-1-113002-4 (Mar. 21, 2006).
Kuhn et al. "Enhancement of Single-Molecule Fluorescence Using a Gold Nanoparticle as an Optical Nanoantenna." Phys. Review Letters 97, p. 017402-1-017402-4 (Jul. 7, 2006).
Rigneault et al. "Enhancement of Single-Molecule Fluorescence Detection in Subwavelength Apertures." Phys. Review Letters 95, p. 117401-1-117401-4 (Sep. 6, 2005).
Hamann et al. "Molecular fluorescence in the vicinity of a nanoscopic probe." Journal of Chem. Physics 114(19), p. 8596-8609 (May 15, 2001).
Gerard et al. "Nanoaperture-enhanced fluorescence: Towards higher detection rates with plasmonic metals." Physical Review B 77, p. 045413-1-045413-8 (Jan. 17, 2008).
Tam et al. "Plasmonic Enhancement of Molecular Fluorescence." Nano Letters 7(2), p. 496-501 (Jan. 27, 2007).
Eid et al. "Real-Time DNA Sequencing from Single Polymerase Molecules." Science 323, p. 133-138 (Jan. 2, 2009).
Uemura et al. "Real-time tRNA transit on single translating ribosomes at codon resolution." Nature 464, p. 1012-1018 (Apr. 15, 2010).
Wenger et al. "Single molecule fluorescence in rectangular nano-apertures." Optics Express 13(18), p. 7035-7044 (Sep. 5, 2005).
Farahani et al. "Single Quantum Dot Coupled to a Scanning Optical Antenna: A Tunable Superemitter." Phys. Review Letters 95, p. 017402-1-017402-4 (Jun. 28, 2005).
Levene et al. "Zero-Mode Waveguides for Single-Molecule Analysis at High Concentrations." Science 299, p. 682-686 (Jan. 31, 2003).
Cubukcu et al. "Plasmonic laser antenna." Applied Physics Letters 89, p. 093120-1-093120-3 (Aug. 31, 2006).
Fromm et al. "Exploring the chemical enhancement for surface-enhanced Raman scattering with Au bowtie nanoantennas." J. of Chem. Physics 124, 4 pgs. (Feb. 10, 2006).
Fromm, David. Stanford University, Dept. Chemistry Thesis—Chapter 6: "Elucidating the mechanism of surface-enhanced Raman scattering with bowtie nanoantennas." From Thesis entitled: *Improving the size mismatch between light and single molecules using metallic nanostructures*, p. 179-211 (2006) OCLC No. 70243173.
Kinkhabwala, Anika. Stanford University, Dept. of Applied Physics Thesis—Chapter 4: "Fluorescence Spectroscopy at High Concentrations using Gold Bowtie Nanoantennas." From Thesis entitled: *Coupling fluorophores molecules to nanophotonic structures*, p. 73-89 (2006) Cat. No. 8714890.
Muskens et al. "Strong enhancement of the radiative decay rate of emitters by single plasmonic nanoantennas." Nano Letters 7(9), p. 2871-2875 (Aug. 7, 2007).
Kinkhabwala et al. "Large single-molecule fluorescence enhancements produced by a bowtie nanoantenna." *Conference Paper*, Frontiers in Optics, San Jose, CA (Oct. 11-12, 2009) 2 pgs. FMH2.pdf.
Kinkhabwala et al. "Large single-molecule fluorescence enhancements produced by a bowtie nanoantenna" and "Supplementary Information." Nature Photonics, 12 pgs. (Oct. 18, 2009). Filed as Appendices A-B in the underlying provisional patent application.
C. Davis. "Fluorescence Molecules in a tight spot." Nature Photonics 3, p. 608-609 (Nov. 2009). Filed as Appendix C in the underlying provisional patent application.
Kinkhabwala et al. "Fluorescence Correlation Spectroscopy at High Concentrations using Gold Bowtie Nanoantennas." Chemical Physics 406, 19 pgs. (Oct. 2012). Filed as part of Appendix D in the underlying provisional patent application.

\* cited by examiner

ENHANCEMENT OF MOLECULAR EMISSION USING OPTICAL-ANTENNA STRUCTURES

RELATED DOCUMENTS

This patent document claims benefit under 35 U.S.C. §119 to U.S. Provisional Patent Application Ser. No. 61/393,709, entitled "Enhancement of Molecular Emission by Bowties Nanoantennas" and filed on Oct. 15, 2010; this patent document and the Appendices filed in the underlying provisional application, including the references cited therein, are fully incorporated herein by reference.

FEDERALLY-SPONSORED RESEARCH AND DEVELOPMENT

This invention was made with Government support under contracts 0507296 and 0425897 awarded by the National Science Foundation. The Government has certain rights in this invention.

BACKGROUND

Nano-emitters such as single molecules are several orders of magnitude smaller than the wavelength of visible light. Therefore, the selection of single nano-emitters and the control of light-molecule interaction processes, including fluorescence efficiency, can be desirable for certain applications. To this end, one approach is to use optical nano-antennas to enhance electric fields and thus improve emission, but achieving reliable fluorescence enhancements is still an ongoing challenge.

Efforts to address this challenge have included use of antenna-like structures, sometimes referred to as optical antennas. While antennas are more commonly appreciated as the transmitting/receiving (or transceiving) conductive structures at the end-point components in radio communication and broadcasting systems, aspects of the present disclosure are directed to optical antennas which are configured to produce significant and/or optimal enhancements to the electric field when illuminated at resonant wavelengths. By using precise nanofabrication technology such as electron- and ion-beam lithography, these optical antennas can be manufactured to operate in the visible region of the spectrum.

SUMMARY

Aspects of the present disclosure relate generally to enhancement of fluorescence and methods relating to the applications discussed above.

One aspect of the present disclosure relates to fluorescence enhancement. In certain embodiments of the present disclosure, an enhancement (up to a factor of 1340 times) of a low-quantum efficiency fluorophore's emission is achievable by coupling the molecule to plasmonic gold bowtie nano-antennas. The gold bowtie nano-antenna greatly enhances the absorption and emission of a weakly emitting fluorophore. This allows for a single molecule to be measured above the signal from 1,000 background molecules, resulting in high sensitive detection in otherwise crowded environments.

The instant disclosure includes an apparatus which has a nano-antenna. The nano-antenna is characterized as having at least two conductive end portions on a transparent support structure. In various embodiments, the end portions manifest metal characteristics (i.e., metallic end portions) in the form of a metallic compound or metal alloy. For example, the metallic end portions include at least one of gold, aluminum, silver, and copper by ion doping or metallic-material deposition. The nano-antenna includes a gap between the at least two portions. The nano-antenna is designed so that a fluid solution of fluorescent molecules can reside in the gap. In embodiments including the fluid solution, fluorescent molecules are suspended in a fluid solution. The fluorescent molecules can be characterized as low-quantum efficiency-type molecules. In other instances, the fluorescent molecules are of a high concentration. Further, the low-quantum efficiency-type molecules can be at a high concentration. The apparatus can also include a photon-counting element that is designed to sense spectral waveforms, characterized as either life-time or broad peaking, due to fluorescence of the fluorescent molecules.

According to certain embodiments, the present disclosure is directed to optical antennas which are configured and arranged to resemble a bowtie. In this example context, a "bowtie antenna" has two triangular metal regions that face each other, tip to tip, with a small dielectric gap between them. The precise shape (e.g., triangular) is not as important as the close proximity of the two inwardly-facing metallic end portions, or tips. In specific applications of such embodiments, the inwardly-facing end portions are sharp. For example, when the end portions or tips are closely spaced, they can be illuminated by a uniform electromagnetic field (e.g., by a broad laser beam), to cause an accumulation of negative charges on one tip and an accumulation of positive charges (electrons are pushed away) on the other tip, and this arrangement of charges changes to the opposite signs when the electromagnetic field changes by one-half cycle of oscillation. Due to the Coulomb attraction between the opposite charges across the dielectric gap that separates the inwardly-facing tips, and the confinement of charge motions by the sharp tips, the electric field in the gap region is enhanced.

The instant disclosure also includes a method of using an optical imaging apparatus that includes providing a fluid solution of low-quantum efficiency-type fluorescent molecules around a nano-antenna. The fluid solution can also be of a high concentration of fluorescent molecules, or can be of a high concentration of low-quantum efficiency-type fluorescent molecules. The nano-antenna has at least two metallic end portions on a transparent support structure, which are arranged to include a gap between the at least two portions. The method further details generating an electric field, due to opposing charges via the at least two metallic end portions, in response to receiving optical energy, and enhancing the electric field and fluorescent emission of the fluorescent molecules in a fluid solution in response to receiving the optical energy. The method further is characterized by sensing lifetime of fluorescence emission or broadly peaking characteristics of spectral waveforms of the fluorescent molecules using a photon-counting circuit.

Also included is a method of manufacturing an optical imaging apparatus, which is characterized by providing a transparent support structure, and depositing a nano-antenna on the support structure. The nano-antenna includes at least two portions and a gap between the at least two portions. The manufacturing also includes surrounding the nano-antenna with a fluid solution of a high concentration of low-quantum efficiency-type fluorescent molecules.

In certain embodiments, combining a low-quantum efficiency-type molecule with a bowtie nano-antenna allows for measurement of a signal from a single molecule in a volume including a number of other unenhanced molecules in a diffraction-limited volume under illumination. The single molecule is detected above the background of many other molecules.

The above overview is not intended to describe each illustrated embodiment or every implementation of the present disclosure.

DESCRIPTION OF THE DRAWINGS AND EXAMPLE EMBODIMENTS

Various example embodiments may be more completely understood in consideration of the following description in connection with the accompanying drawings, in which.

Figure 1A:
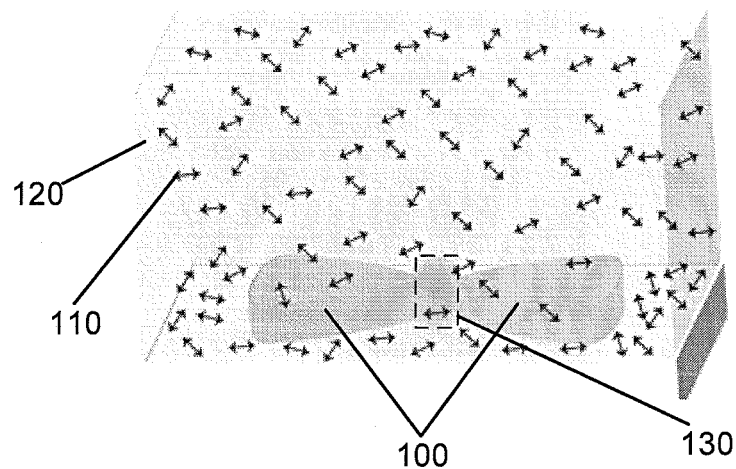
FIG. 1A shows a example embodiment of an apparatus in accordance with the instant disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the scope of the present disclosure including aspects defined in the claims.

DETAILED DESCRIPTION

Aspects of the present disclosure may be more completely understood in consideration of the detailed description of various embodiments of the present disclosure that follows in connection with the accompanying drawings. The embodiments and specific applications discussed herein may be implemented in connection with one or more of the above-described aspects, embodiments and implementations, as well as with those shown in the figures and described below.

In an example embodiment of an apparatus of the instant disclosure, the apparatus includes a nano-antenna having at least two metallic end portions on a transparent support structure. The at least two metallic end portions, in a specific embodiment, are doped with metal ions. In another embodiment, the at least two metallic end portions are made of gold, aluminum, silver, or copper. The nano-antenna of the instant embodiment is designed with a gap between the at least two metallic end portions, where a fluid solution of fluorescent molecules can reside. The nano-antenna of this embodiment, is further characterized in that it can receive and respond to optical energy by generating an electric field, which is due to opposing charges via the at least two metallic end portions, and enhances the electric field and fluorescence emission of the fluorescent molecules in the fluid solution when the fluid solution resides between the at least two metallic end portions. Further, in the instant embodiment, the apparatus includes a photon-counting circuit designed to sense excited state life-time or broadly peaking characteristics of spectral waveforms due to the fluorescence of the fluorescent molecules. In certain specific embodiments, the photon-counting circuit senses the life-time characteristics of the emission from the fluorescent molecules. In other embodiments, the photon-counting circuit is configured and arranged to sense broadly peaking characteristics of the spectral waveforms, in which the peaking characteristics of the fluorescence spectrum are exemplified by clusters of peaks over a span of the spectral waveform as opposed to Raman-like characteristics in which sharp (and spectrally-separated) peaks are proportional to the electric field.

The photon-counting circuit of the instant embodiment can be, for example, an avalanche photodiode or a photomultiplier connected to a Picoharp 300 (or an acceptable commercially available photon-sensing apparatus capable of time-correlated single-photon counting). In certain specific embodiments, the nano-antenna is characterized as a gold bowtie, or a bowtie fashioned from metals with high conductivity such as aluminum, silver, and copper. In certain specific embodiments, the at least two metallic end portions are doped with copper ions. In certain other embodiments, the fluorescent molecules, which the apparatus is designed to contain, are low-quantum efficiency-type molecules. The low-quantum efficiency-type molecules, for example, are have a quantum efficiency ($\eta_0 = [k_{rad,0}/(k_{rad,0}+k_{nonrad,0})]$) of approximately 2.5% or less than 25%. Low quantum efficiency molecules add the additional enhancement of fluorescence because the bowtie effectively enhances emission due to the oscillating molecular dipole that makes the electrons in the bowtie shake, and therefore emit. In other specific embodiments, the fluorescent molecules that can reside in the apparatus are highly concentrated (e.g., up to 200 µM which produces 1,000 background molecules in a diffraction-limited volume centered on the bowtie).

In certain embodiments, the apparatus described can further include a fluid solution of fluorescent molecules, the fluorescent molecules being highly-concentrated or a low-quantum efficiency-molecule type in or around the gap between the at least two portions.

In another specific embodiment, the apparatus can further include one, or more, of the following elements: a highly-concentrated fluid solution of fluorescent molecules in or around the gap between the at least two metallic end portions; and a fluid solution of low-quantum efficiency-type molecule fluorescent molecules in or around the gap between the at least two metallic end portions. Moreover, this example embodiment includes a photon-counting circuit designed to sense spectral waveforms due to fluorescence of the stimulated fluorescent molecules.

Additionally, certain embodiments of the apparatus, described above, can have a light emitting element. The light emitting element, of the instant embodiment, is designed to stimulate the fluorescent molecules from a ground state to an excited state to enable fluorescence emission.

In certain other specific embodiments of the apparatus, the apparatus also has a light emitting element, which produces pulsed light designed to stimulate fluorescent molecules for the purpose of measuring the time delay between excitation by the light emitting element and the emission of fluorescent molecules for the purpose of determining life-time characteristics. In other embodiments, the apparatus includes a light emitting element designed to stimulate a high concentration of fluorescent molecules.

In another example embodiment, an apparatus, which includes a bowtie nano-antenna, is designed. The bowtie nano-antenna has at least two metallic end portions on a support structure, and is configured with a gap between the at least two metallic end portions where a fluid solution of low-quantum efficiency-type molecules reside. In certain specific embodiments, a high concentration of low-quantum efficiency-type molecules is present in the fluid solution. The bowtie nano-antenna of the instant embodiment is further configured to receive and respond to optical energy by generating an electric field due to opposing charges via the at least two metallic end portions. Moreover, the bowtie nano-antenna is designed to enhance the electric field and fluorescence emission of the fluorescent molecules in the fluid solution when the fluid solution resides between the at least two metallic end portions.

In another example embodiment, an apparatus having a bowtie nano-antenna is presented. The bowtie nano-antenna has at least two metallic end portions on a support structure, and is designed with a gap between the at least two metallic end portions where a fluid solution of a high concentration of fluorescent molecules reside. In certain specific embodiments, the high concentration fluorescent molecules are characterized as low-quantum efficiency-type molecules. Further, in this example embodiment, the bowtie nano-antenna is designed to receive, and respond to, optical energy by generating an electric field due to opposing charges via the at least two metallic end portions, and enhance the electric field and fluorescence emission of the fluorescent molecules in the fluid solution when the fluid solution resides between the at least two metallic end portions.

The instant disclosure is also directed towards a method of using an apparatus. For example, a method of using an apparatus includes providing a fluid solution of fluorescent molecules, characterized as low-quantum efficiency-type molecules, in a gap between at least two metallic end portions of a nano-antenna (which is supported by a support structure). Further, the method described here involves generating an electric field due to opposing charges via the at least two metallic end portions in response to receiving optical energy, and enhancing the electric field and fluorescence emission of the low-quantum efficiency-type molecules in the fluid solution in response to receiving the optical energy. Moreover, the method involves sensing life-time or broadly peaking characteristics of spectral waveforms of the low-quantum efficiency-type molecules using a photon-counting circuit. In certain specific embodiments, the low-quantum efficiency-type molecules are of a high concentration.

In another example embodiment, a method of using an apparatus is detailed by providing a high concentration of fluorescent molecules in a fluid solution in a gap between at least two metallic end portions of a nano-antenna, the nano-antenna being supported by a support structure. In certain specific embodiments, the high concentration of fluorescent molecules are characterized as low-quantum efficiency type molecules. The method also includes generating an electric field due to opposing charges via the at least two metallic end portions in response to receiving optical energy. Further, the method is characterized by enhancing the electric field and fluorescence emission of the high concentration of fluorescent molecules in a fluid solution in response to receiving the optical energy; and sensing life-time or broadly peaking characteristics of spectral waveforms of the low-quantum efficiency-type molecules using a photon-counting circuit.

In certain embodiments, combining a low-quantum efficiency-type molecule with a bowtie nano-antenna allows for measurement of a signal from a single molecule in a volume including a number of other unenhanced molecules in a diffraction-limited volume under illumination. The single molecule is detected above the background of many other molecules.

In certain more specific embodiments, fluorescence correlation spectroscopy ("FCS") is used to detect the fluorescence of a molecule. In such embodiments wherein FCS requires only one fluorescent molecule diffusing through a diffraction-limited volume at any time, the use of a bowtie can allow for isolation and enhancement of a single molecule when there are many molecules diffusing through the same diffraction-limited volume. The enhancement achieved by the bowtie also allows for the detection of fluorescent molecules that are normally too dim to measure. This allows for greater flexibility in fluorescent molecule design and the detection of small numbers of weakly emitting labeled biomolecules, for example.

Figure 1B:
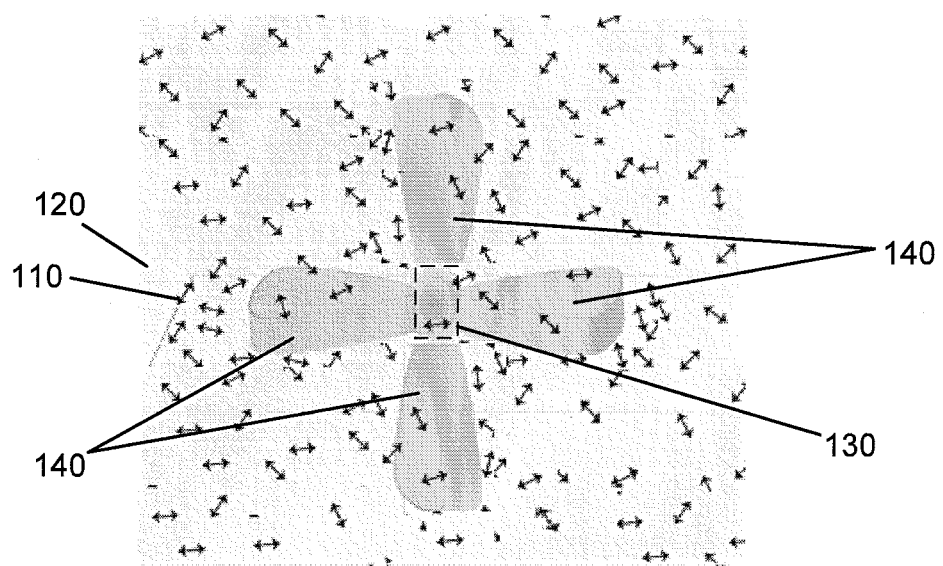
FIG. 1B shows another example embodiment of an apparatus in accordance with the instant disclosure.

Turning now to the figures, FIGS. 1A and 1B show an apparatus in accordance with an example embodiment. FIG. 1A shows the apparatus, which includes a nano-antenna 100 of at least two metallic end portions. FIG. 1A shows a nano-antenna 100 having two metallic end portions shaped and arranged in a bowtie-like manner. The nano-antenna structure 100 can be made of gold or another acceptable metal (e.g., silver, aluminum, copper). Additionally, the nano-antenna structure 100 can be doped with metal (e.g., copper) ions. In another example embodiment shown in FIG. 1B, the nano-antenna 140 has four portions. The embodiment shown in FIG. 1B is similar to a double bowtie-like structure. Turning again to both FIGS. 1A and 1B, nano-antenna 100/140 of the apparatus shown includes a gap 130 between the at least two portions. In the embodiment shown, the gap 130 of the nano-antenna 100/140 is designed so a fluid solution 120 of fluorescent molecules 110 can reside. The nano-antenna 100/140 is supported by a transparent support structure. The fluorescent molecules 110 in the fluid solution 120 can be a high concentration, or low-quantum efficiency-type, or a high concentration of low-quantum efficiency-type molecules.

Figure 2A:
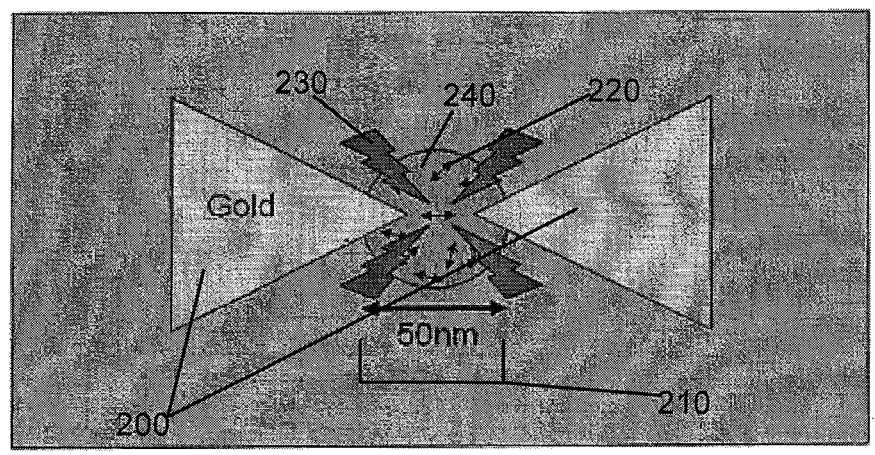
FIG. 2A shows a top-down view of an apparatus based on an example embodiment.
Figure 2B:
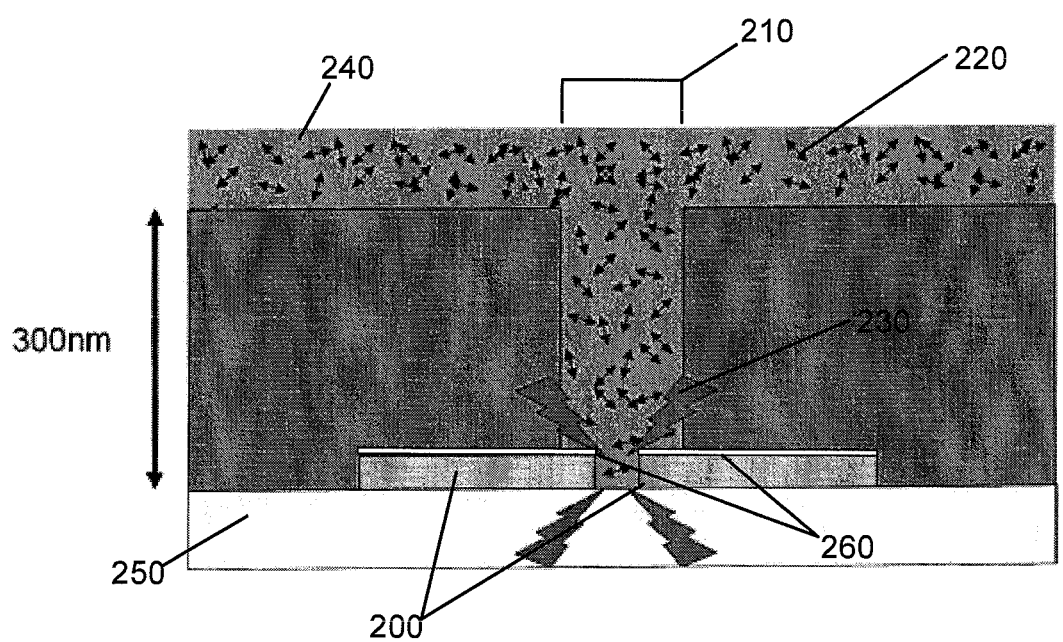
FIG. 2B shows a side-view of an apparatus based on an example embodiment.

Turning now to FIGS. 2A and 2B, which respectively show a top-down and side view, respectively, of another example embodiment of the apparatus. The apparatus includes a bowtie nano-antenna 200 that has at least two metallic end portions on a transparent structure 250. The nano-antenna 200 is designed to include a gap 210 between the at least two metallic end portions. Further, the apparatus is designed where a fluid solution 240 of fluorescent molecules 220 (e.g., low-quantum efficiency-type molecules) can reside in the nano-antenna gap 210. Often, the fluid solution 240 contains a high concentration of fluorescent molecules 220. In certain instances, the fluorescent molecules 220 are a high concentration of low-quantum efficiency-type molecules. When stimulated, the fluorescent molecules 220 emit spectral waveforms 230. In certain instances, a transparent dielectric material 260 is fabricated on top of the bowtie structure to limit the region where the fluid may flow.

Figure 4:
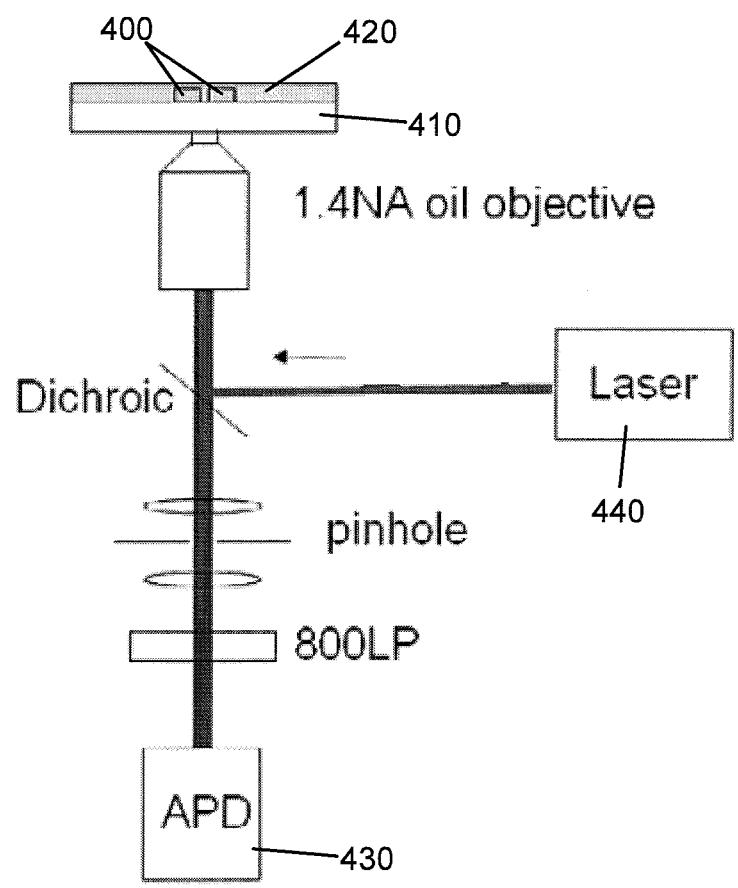
FIG. 4 shows an example embodiment of an apparatus in accordance with the instant disclosure.

FIG. 4 shows an apparatus of another example embodiment. The apparatus shown in FIG. 4 includes a nano-antenna 400 on a support structure 410. The nano-antenna 400 (e.g., a gold bowtie-like structure) of the instant embodiment includes at least two metallic end portions arranged around a gap. The apparatus is designed so a fluid solution 420 of fluorescent molecules can reside in the gap. In certain embodiments, the apparatus further has a light emitting element 440, which is designed to stimulate the fluorescent molecules in the fluid solution 420. Moreover, the apparatus has a photon-counting circuit 430 that can sense spectral waveforms due to fluorescence of the stimulated fluorescent molecules in the fluid solution 420. In certain embodiments, the photon-counting element 430 is configured and arranged to sense a broadly peaking spectral fluorescence response of the fluorescent molecules. In other embodiments, the photon-counting element 430 senses the life-time of the emission of the fluorescent molecules. Further, in yet another embodiment, the light emitting element 440 is capable of emitting various wavelengths of light. In certain embodiments, the light emitting element 440 is capable of emitting pulsed light.

In certain embodiments, the fluid solution 420 includes low-quantum efficiency-type molecules. In other embodiments, the fluid solution 420 includes a high concentration of fluorescent molecules. In yet another set of embodiment, the fluid solution 420 includes a high concentration of low-quantum efficiency-type molecules.

Experimental Embodiments

A 780-nm continuous-wave diode laser or a pulsed titanium sapphire laser is used to excite fluorescence from the fluorescent TPQDI molecules in a confocal microscope. Appropriate excitation and emission filters ensured that only TPQDI fluorescence reached the avalanche photodiode (APD) photon-counting silicon detector. Essentially all fluorescent molecules irreversibly photobleach after a certain number of excitation cycles due to photo-degradation (for example, photo-oxidation), so each spot in the image of the emission was observed until single-step digital photobleaching occurred to ensure it corresponded to a single unenhanced TPQDI molecule. Each molecule's dipole moment is randomly oriented with respect to the linear excitation field polarization, so each spot has a different brightness, with the brightest spots arising from molecules with dipole moments aligned along the excitation polarization. To measure the brightness of an unenhanced molecule for which the dipole moment is oriented along the excitation field, $S_{un,max}$, 201 single molecules were measured and the intensities of the brightest five were averaged, yielding 2.3 detected photons per 10 ms integration time per mW excitation power.

Due to the size mismatch between light and nano-scale objects like single molecules, it is important to study and ultimately control light-molecule interactions. Plasmonic nano-antennas create highly enhanced local fields when pumped resonantly, but whether they enhance or quench fluorescence depends upon a variety of factors. A single fluorescent molecule (SM) with transition dipole $\vec{\mu}$ acts as a nano-scale optical sensor of the local field $\vec{E}$ near a bowtie because its transition rate is proportional to $|\vec{\mu} \cdot \vec{E}|^2$, while its emission either couples to the far field via the bowtie or quenches via Ohmic losses due to currents in the metallic nano-antenna. Low-quantum efficiency (QE) emitters can have high fluorescence enhancements ($f_F$), because their intrinsic QE has the potential to be improved by the antenna's presence. Using the highly enhanced optical fields of gold bowties to enhance a low QE emitter, large $f_F$'s are observed due to enhanced absorption as well as an increased radiative emission rate, resulting in enhancement of the molecule's emission rate to the far-field, intrinsic QE, despite additional non-radiative Ohmic effects.

Another aspect of the present disclosure involves placing a molecule in the gap of a bowtie nano-antenna, which is formed by two metallic triangles placed tip to tip with a small gap on a transparent substrate. This has been demonstrated to produce a very large enhancement of the emission from a single molecule, as discussed below.

Figure 3:
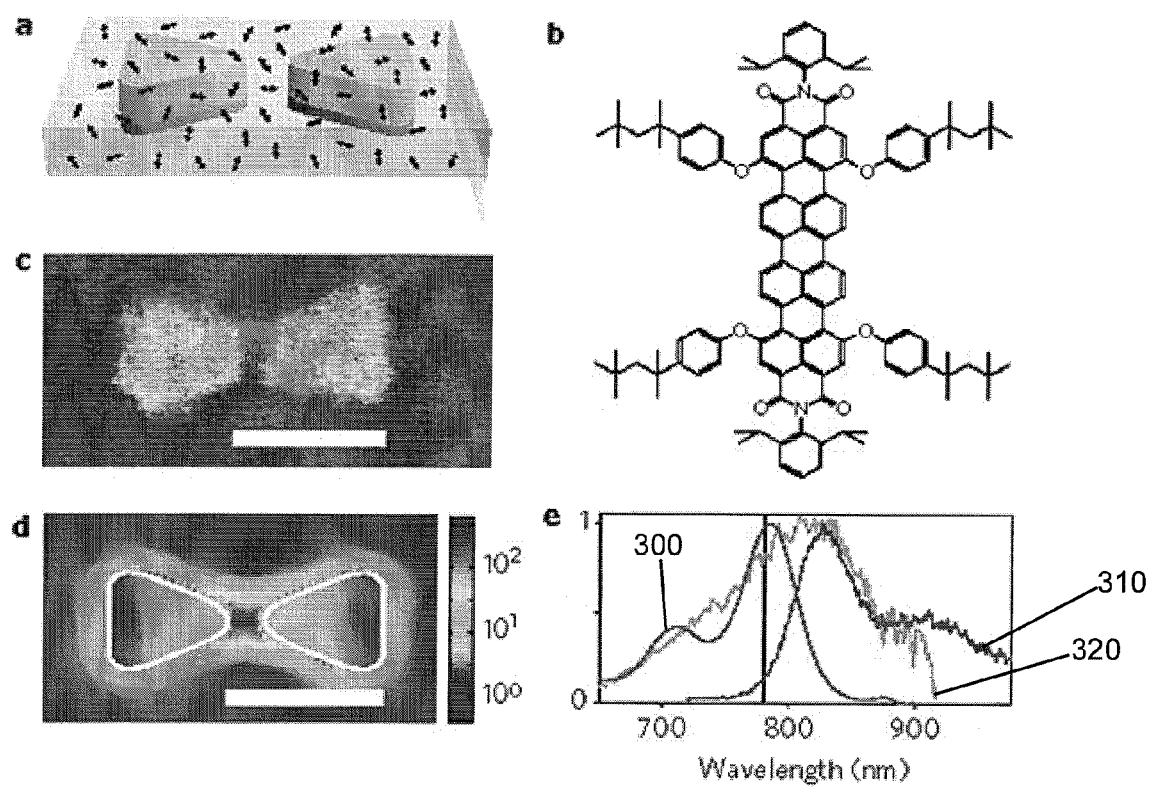
FIG. 3A shows an example embodiment of a bowtie nano-antenna in a solution of fluorescent molecules.
FIG. 3B shows the molecular structure of a fluorescent molecule.
FIG. 3C shows a scanning electron microscope image of a bowtie nano-antenna with a 100 nm scale bar.
FIG. 3D shows a local intensity enhancement estimation of fluorescent molecules surrounding a bowtie nano-antenna with a 100 nm scale bar.
FIG. 3E shows the absorption and the emission spectra of fluorescent molecules as well as the scattering spectrum for the bowtie nano-antenna of FIG. 3C.

Experimental measurements of $f_F$ for a single molecule, consistent with an embodiment of the present disclosure, were performed by coating electron-beam fabricated gold bowtie nano-antennas, shown in FIG. 3C, with the relatively low fluorescence QE ($\eta_{10}$~2.5%) near-IR dye TPQDI (N,N'-bis(2,6-diisopropylphenyl)-1,6,11,16-tetra-[4-(1,1,3,3-tetramethylbutyl)phenoxy]quaterrylene-3,4:13,14 bis(dicarboximide)), shown in FIG. 3B, doped in a thin poly(methyl methacrylate) (PMMA) layer covering the bowtie, as seen in FIG. 3A. In addition to a low QE, FIG. 3E shows TPQDI's absorption 300 and emission 310 spectra overlap well with the bowtie plasmon resonance 320. FIG. 3D shows an electromagnetic calculation of the local optical field enhancement produced by the bowtie.

Figure 5:
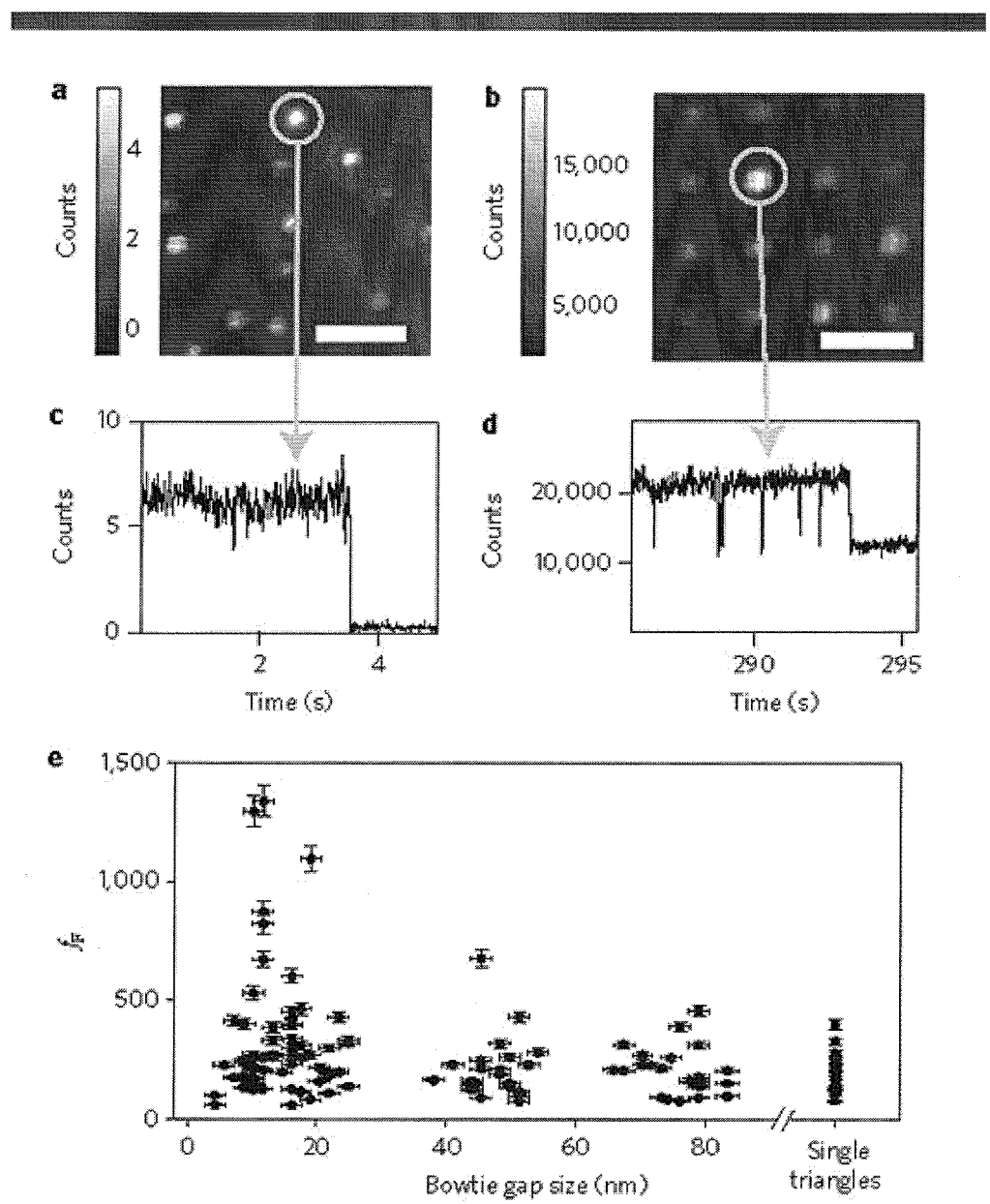
FIG. 5A shows a spatial fluorescence scan of a low concentration of fluorescent molecules without a bowtie nano-antenna with a 4 micrometer scale bar.
FIG. 5B shows a spatial fluorescence scan of 16 bowtie nano-antennas coated with a high concentration of fluorescent molecules with a 4 micrometer scale bar.
FIG. 5C shows a fluorescence signal as a function of time for a single position of the fluorescence scan of FIG. 5A.
FIG. 5D shows is a fluorescence signal as a function of time for one position of the fluorescence scan of FIG. 5B
FIG. 5E shows a scatter plot of fluorescence brightness enhancements as a function of bowtie gap size.

FIG. 5A shows a confocal fluorescence scan from a thin PMMA film with low TPQDI concentration on a transparent substrate without bowtie nano-antennas, where each spot in the image arises from the emission from a single unenhanced TPQDI molecule, verified by single-step digital photobleaching, as seen in FIG. 5C. Each molecule's dipole moment is randomly oriented with respect to the linear excitation field polarization, so each SM has a different brightness—the brightest of which have their dipole moments aligned with the excitation polarization. In order to measure the brightness of an unenhanced molecule aligned along the excitation field, $S_{un,max}$, 201 SM's were measured and the intensities of the brightest 5 were averaged together.

FIG. 5B shows a confocal scan from an array of 16 bowties coated with a high concentration of TPQDI in PMMA (~1, 000 molecules/diffraction limited spot or ~3 molecules/(10 nm)$^2$). The linear polarization of the excitation light was aligned along the line between the two triangles of the bowties. In order to see a single molecule out of the many surrounding the bowtie, the fluorescence as a function of time is measured, the results of which are shown in FIG. 5D. Discrete blinking and eventual photobleaching of 50% of the total signal can be attributed to a single molecule's dynamics and reveal that half of the fluorescence from this particular bowtie is due to a single molecule. The digital (step-like) sudden drop near 293 seconds is an unambiguous signature that a single molecule photobleached, and the step size shows its contribution to the total signal, $S_{bowtie}$. While the exact position and orientation of this single molecule is unknown, it is clear that this molecule is located near the position of maximum field enhancement, i.e., between the two triangle tips, as seen in FIG. 3D. The fluorescence enhancement factor $f_F$ for this single molecule was determined with $f_F=(S_{bowtie}-P_{un})/(S_{un,max}P_{bowtie})$, where $S_{bowtie}$ and $P_{bowtie}$ are the single molecule fluorescence signal and laser excitation power used for FIG. 5B, while $S_{un,max}$ and $P_{un}$ apply to FIG. 5A.

The fluorescence brightness enhancement factor, $f_F$, is calculated by comparing the rate of photon emission from a single molecule (SM) coupled to a bowtie nano-antenna measured from the fluorescence drop upon photobleaching to the rate from a single molecule far from a bowtie scaled to equivalent pumping intensities. This method of linear scaling relies on the fact that no saturation of the emission occurred. To identify the brightness expected from a molecule perfectly aligned with the pumping polarization, many confocal scans of a dilute TPQDI doped PMMA sample (<1 molecule/diffraction limited spot) without bowtie nano-antennas were measured. Each SM spot was fit to a 2-D Gaussian to find the molecule's spatially integrated detected photons above background, and only molecules that had brightnesses greater than 60 counts/10 ms were considered (201 molecules). Due to the random orientation of the dipole moment with respect to the linearly polarized excitation beam, a distribution of brightnesses is to be expected. The 5 brightest molecules were averaged together to find the brightness expected from a single molecule aligned along the excitation polarization direction and away from a bowtie.

The local field enhancement is highly dependent on the bowtie gap size. A number of bowties with different gap sizes were measured, searching for highly enhanced molecules. FIG. 5E is a plot of $f_F$ for 129 SM's and shows that the smallest gap bowties yielded the highest $f_F$'s, up to a factor of 1340 times, consistent with smaller gap bowties having higher local field strengths. A broader distribution of $f_F$ values occurs because not all molecules are optimally located. Nevertheless, the molecule that is oriented and located in the center of the gap experiences a significant emission enhancement.

Figure 6:
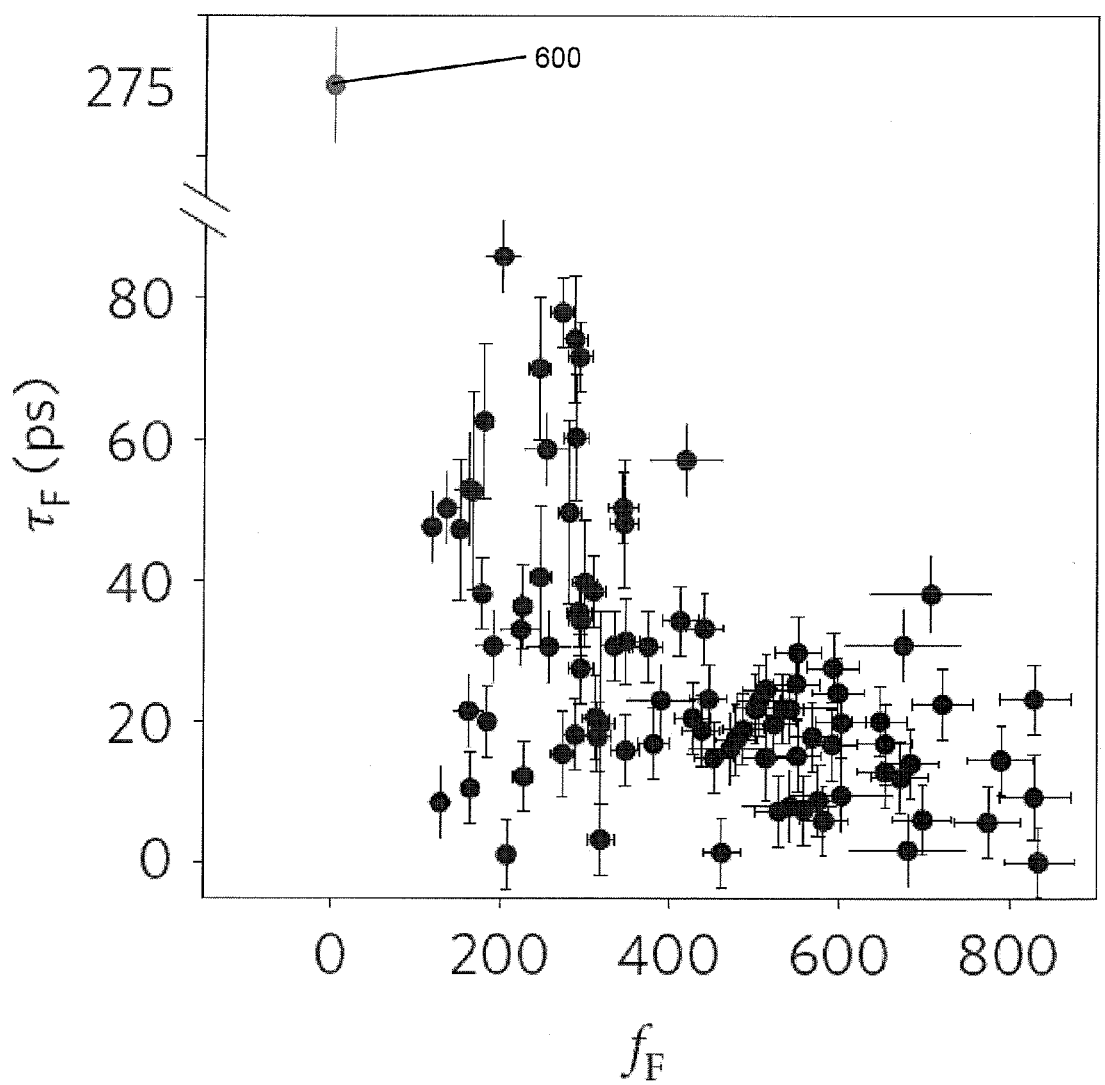
FIG. 6 shows a scatter plot of measured decay lifetime versus brightness enhancement for fluorescent molecules on bowtie nano-antennas.

In addition to the brightness enhancement, the molecule's emission rate is also highly enhanced. This is assessed by measuring the excited state lifetime of the emission from the molecule under pulsed excitation by standard methods of time-correlated single-photon counting. Measured values of excited state lifetime and observed brightness enhancements for each single molecule are shown in FIG. 6. The point 600 is the ~275 ps lifetime of TPQDI molecules not coupled to any bowtie. The single molecules interacting with the bowtie the strongest have lifetimes well below 20 ps, and many have lifetimes at our detection limit of 10 ps. Thus, the spontaneous emission rate for the molecules is enhanced by up to ~40 times. This property is useful in cases where very high emission rates are needed (e.g., single-photon sources).

According to certain embodiments of the present disclosure, bowties are used to enhance the fluorescence of a single molecule by a factor of 1340. This enhancement equates to the ability to pick out a single molecule's fluorescence from a background of >1,000 unenhanced molecules. Based on such levels of enhancement, certain embodiments use bowtie nano-antennas as sensors in crowded environments, where only the signal from a small number of molecules in a nanoscale region is detected.

Figure 7:
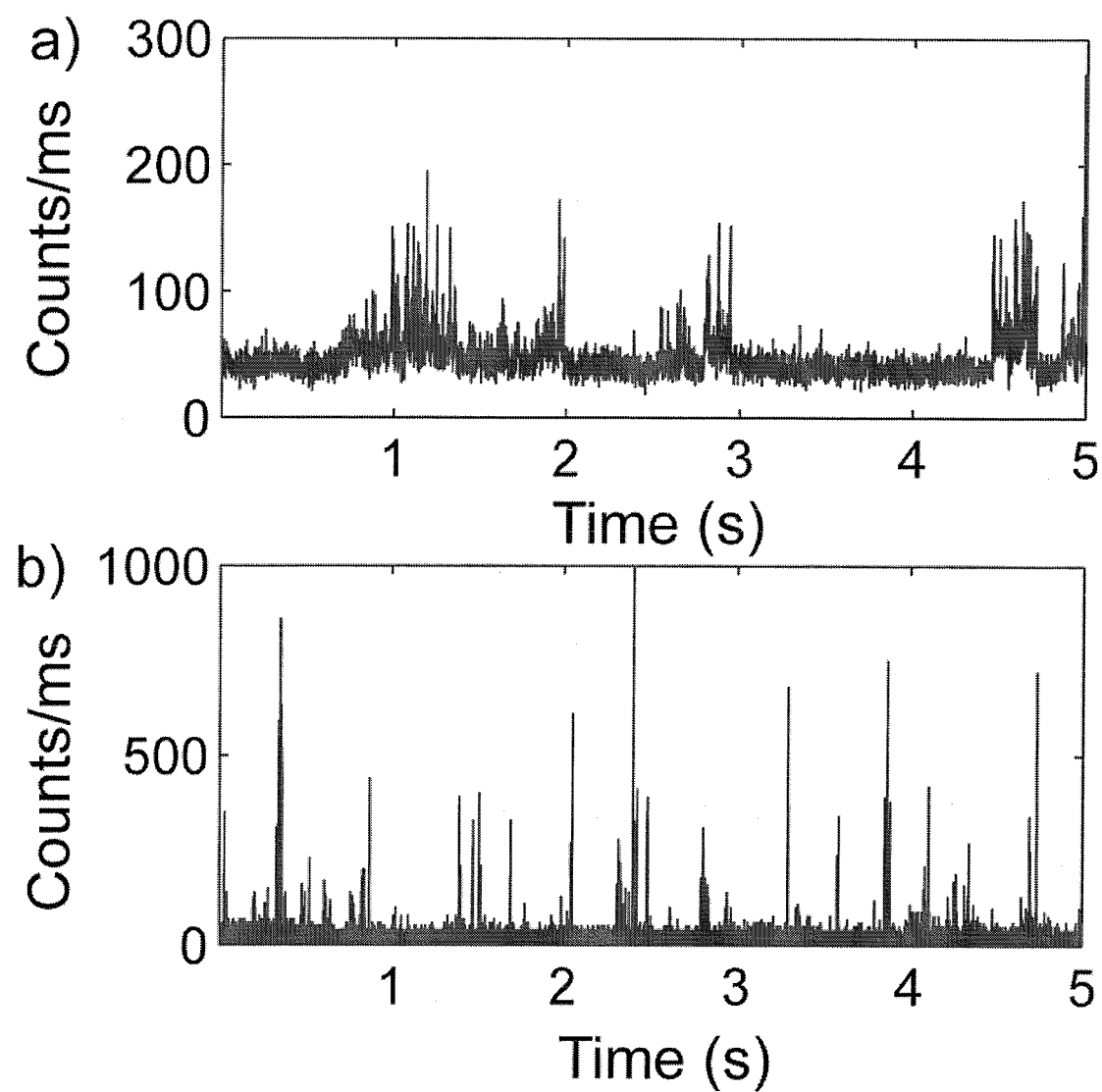
FIG. 7 shows fluorescence time traces binned to 1 ms for a bowtie immersed in ethanol and water containing fluorescent molecules.

Also according to the present disclosure, an apparatus exists for measuring enhanced fluorescence from a single molecule or a very small number of molecules in a concentrated sample of solution. The apparatus can be in the form of a bowtie, which can be fabricated with electron-beam (E-beam) lithography onto a quartz coverslip. If desired, a new layer of the E-beam resist PMMA (poly(methyl methacrylate)) can be spun onto the sample with a thickness of ~300 nm or greater. The PMMA can be exposed and developed in an E-beam step only over the bowtie's gap region, leaving behind 50 nm or smaller diameter holes centered on each bowtie's gap. A concentrated solution can then be placed onto the sample, filling these holes. The fluorescence as a function of time dramatically changes as molecules move into and out of the enhanced region in the bowtie's gap. By reducing the volume of solution in the confocal volume using the PMMA overcoat, even higher concentrations of molecules can be used since the signal from a single enhanced molecule is more easily detected in the presence of the background signal from unenhanced molecules. Any out-of-focus fluorescence from molecules in the solution above the PMMA film is rejected by the usual confocal collection pinhole, that is, the collected fluorescence is imaged through a pinhole in a conjugate image plane. In this way, one molecule or a small number of molecules can be sensed even in very highly concentrated solutions. However, the presence of the PMMA overcoat is not a requirement of this invention. Without any PMMA overcoat, the enhancement of the emission from fluorescent molecules near the bowtie gap enables flashes of emission from single molecules to be detected, as shown in FIG. 7, discussed further below.

Local field enhancement is highly dependent on bowtie gap size. A variety of bowtie sizes were investigated in arrays consisting of 49 bowties or single triangles with the same E-beam lithography pattern. Confocal scans were taken of each antenna array and the five brightest spots in any array measured as a function of time to look for highly enhanced molecules as determined by significant single photobleaching steps. The gap sizes were then measured by scanning electron microscopy (SEM). The bowties with smallest gaps yielded the highest $f_F$ values, up to a factor of 1,340, consistent with bowties with smaller gaps having higher local field strengths than larger gap bowties and single triangles. A broader distribution of $f_F$ values occurs because not all molecules are optimally located as in FIG. 5E.

The optical behavior of the bowtie nano-antenna can be simulated by solving Maxwell's equations using the three-dimensional finite-difference time-domain (FDTD) method. The refractive indexes of gold and the thin titanium sticking layer were modeled by a fit to tabulated experimental data using the method of complex-conjugate pole-residue pairs.

To simulate the excitation process, plane waves polarized in the x-direction were incident from the quartz side. The optical intensity enhancement factor driving the increased absorption rate $f_E$ was then obtained by comparing the electric field intensities with and without the metallic bowtie. At a wavelength of 780 nm, the enhancement $f_E$ was 181 in the center of the bowtie gap, and the maximum field enhancement occurs at the two gold tips.

To simulate the emission process, a point current source is placed in the gap region. In the presence of the bowtie antenna, the radiated power $P_r$ into the far field and the power dissipated in the metal $P_{nr}$ were calculated. The enhancement factors were then obtained by normalization with respect to the radiated power $P_0$ of the same point current source in the absence of the antenna. As a result, for a point current source polarized in the x-direction at the center of the gap emitting at 820 nm, the radiative factor was $f_r \equiv P_r/P_0 \equiv 187$ and the non-radiative factor $f_{nr} \equiv P_{nr}/P_0 \equiv 578$. In the vicinity of the antenna, the non-radiative process due to metal loss thus dominates the radiative process, resulting in a quantum efficiency ($P_r/(P_r + P_{nr})$) of approximately 25%.

Based on the simulations above it is possible to estimate the fluorescence enhancement factor. The unenhanced molecule has a low intrinsic fluorescence quantum efficiency of $\eta_0 = [k_{rad,0}/(k_{rad,0}+k_{nonrad,0})] = 2.5\%$, because its intrinsic non-radiative decay rate $k_{nonrad,0}$ dominates over its intrinsic radiative decay rate $k_{rad,0}$. The presence of the antenna should enhance the quantum efficiency by a factor $f_\eta = f_r/[(1-\eta_0)+\eta_0 (f_r+f_{nr})] = 9.32$, which, when multiplied by the field enhancement factor to account for the improved excitation ($f_E = 181$) as calculated above, yields a total fluorescence enhancement ratio $f_F = f_E f_\eta = 1,690$. This number is in good agreement with the maximum experimentally measured enhancement factor of 1,340, particularly if one takes into account the experimental uncertainty in determining the exact location and orientation of the molecule. The enhancement can be different in different directions. For instance, in the vertical direction (z-direction), the functions are relatively constant in the gap region and fall off quickly above the metal surface. In the gap region, the maximum fluorescence enhancement occurs at the center, and fails closer to the metal tip because of lower quantum efficiencies arising from increased Ohmic losses. The same analysis indicates that a molecule with a high intrinsic quantum efficiency (for example, $\eta > 25\%$) in fact would not have any quantum efficiency enhancement by the same antenna and thus would have a much lower $f_F$.

The discussions above suggest that the enhancement of quantum efficiency should also produce a change in single molecule total decay lifetime, $\Sigma_F$. Excited state lifetime changes for ensembles of molecules coupled to plasmonic structures have been reported previously. For further information regarding such analysis relative to excited state lifetime changes, reference may be made to various publications including, e.g., Muskens, O. L., Giannini, V., Sanchez-Gil, J. A. & Gomez Rivas, J. Strong enhancement of the radiative decay rate of emitters by single plasmonic nanoantennas. Nano Lett. 7, 2871-2875 (2007). To investigate this for single molecules, a mode-locked Ti:Sapphire laser tuned to 780 nm was used in conjunction with a fast time resolution APD (e.g., Micro Photon Devices (MPD) PDM series), and a time-correlated single-photon counting analyzer (e.g., Picoharp 300) to measure total decay lifetime (FIG. 6). The $\tau_F$ value for TPQDI in PMMA in the absence of the antenna is 275 ps. To measure $\tau_F$ for a single molecule on a bowtie despite the presence of background fluorescence from other molecules, all fluorescence photons from the molecule-coated bowtie were time-tagged. Time delay histograms could then be formed for the fluorescence photons before and after a single molecule photobleaching event. The difference in shape of these two time delay histograms is the single molecule's time delay histogram. Deconvolution of the measured instrument response function (IRF) allowed measurement of lifetimes down to 10 ps. Single molecule TPQDI lifetimes shorter than 10 ps were measured for molecules strongly enhanced by the bowties, a factor of ⅛ decrease in $\tau_F$.

Compared to measurements of $f_F$, changes in $\tau_F$ only monitor changes in non-radiative and radiative processes and not changes in absorption. At low $f_F$, both slow and fast $\tau_F$ were observed in the data (FIG. 6). This result is expected because $\tau_F$ depends only upon the radiative and non-radiative rates, but $f_F$ depends also on local intensity, and many combinations are possible for different molecule positions and orientations. To achieve high values of $f_F$, the molecule's absorption and quantum efficiency should be significantly improved, which can occur in the gap where both the radiative and non-radiative rates are larger. Therefore, only short lifetimes are to be expected for high-$f_F$ molecules.

In this demonstration, single molecules of TPQDI were used as probes of $f_F$ near gold bowtie nano-antennas. Using the dominant emission that arises from the most highly enhanced molecule, fluorescence brightness enhancements of up to 1,340 times were observed, in agreement with electromagnetic calculations of radiative, non-radiative and electromagnetic intensity enhancements. Single molecule lifetimes provide additional information about the decay processes for each molecule, independent of the local optical intensity enhancement. The bowtie nano-antenna feature provides a useful balance between enhancement and losses for single molecule emission applications. In particular, emission decay times as short as 10 ps were observed, which means that a high emission-rate, room-temperature, single-photon source can be fabricated using a single molecule in a bowtie gap.

In an example manufacturing embodiment, the bowtie nano-antennas are fabricated using electron-beam lithography onto 50-nm-thick indium-tin-oxide coated quartz coverslips. The fluorescent dye TPQDI is doped into 1% weight/volume of 75,000 $M_W$ PMMA in distilled toluene and spun onto the bowtie sample at 2,500 RPM to achieve a final thickness of 30 nm. The sample was imaged using an inverted confocal microscope (e.g. a Nikon Diaphot200 inverted microscope and a Topometrix closed-loop sample scanning stage) and the signal collected using a silicon avalanche photon-counting detector APD. Continuous-wave measurements of fluorescence brightness enhancement are performed with a 780-nm diode laser, and pulsed measurements of fluorescence lifetime used a mode-locked Ti:Sapphire laser.

For tests in a fluid solution, fluorescence correlation spectroscopy (FCS) test measurements can be performed. In this type of test, a Gaussian-shaped laser beam is focused into a dilute solution of fluorescent molecules. A confocal fluorescence microscope then measures the bright flashes of fluorescence from small numbers or single molecules passing through the diffraction-limited focused laser spot of diameter ~250 nm in the visible. FIG. 7 shows fluorescence time trace binned to 1 ms for a bowtie immersed in (a, upper curve) 1 µM IR800cw in ethanol using 430 W/cm² laser intensity and in (b, lower curve) 1 µM ICG in water using 144 kW/cm² laser intensity. ICG in water has higher contrast between enhanced molecules compared to background than IR800cw in ethanol. The autocorrelation of the fluorescence time trace provides information on any dynamics in the fluorescence signal on time scales shorter than the diffusion time through the laser focus (typically on the order or 1 ms). Examples of processes that affect fluorescence on these time scales are photon antibunching, dark state bottlenecks, photobleaching, conformational dynamics, binding events, Förster resonance energy transfer (FRET), and diffusion and these kinds of measurements have been performed on a number of free dye and labeled biological systems including fluorescent proteins yielding a wealth of information. By exact analysis of the optical configuration, even absolute diffusion coefficients may be extracted. FCS is usually performed at extremely low dye concentrations so that the bursts of fluorescence from single molecules have maximum contrast, but this limits the technique to solutions of 10 pM-1 nM concentrations.

High concentration FCS experiments can be performed by using zero-mode waveguides to confine the illumination volume much further than is possible with normal diffraction-limited confocal microscopy. See, e.g., Levene, M. J. et al. Zero-Mode Waveguides for Single-Molecule Analysis at High Concentrations. Science 299, 682-686 (2003). Zero-mode waveguides consist of sub-wavelength diameter (~70-100 nm) holes in thin aluminum films. Electromagnetic waves cannot propagate through sub-wavelength holes, so there is only a weak penetration of evanescent waves into these apertures, restricting illumination to a few 10's of nm from the substrate. This technique has been utilized to allow FCS experiments at up to 200 µM concentration. The zero-mode waveguide geometry has been extended to implement real-time single-molecule sequencing of DNA, as well as real-time translation of RNA into protein.

Plasmonic nano-antennas can be used to concentrate and enhance electromagnetic fields at optical frequencies and the fluorescence from a molecule located in these localized electromagnetic fields can be far larger than for unenhanced molecules. In particular, gold bowtie antennas, which enhance local $|E|^2$ fields by factors up to 1,000 in a ~(20 nm)$^3$ region, have been shown to enhance a single-molecule's fluorescence by factors up to 1,300. Zero-mode waveguides, however, have only been shown to enhance fluorescence up to 25×. The bowtie structure, being lithographically fabricated, allows the generation of large arrays of repeatable structures, as opposed to the case for an earlier study utilizing localized surface plasmons for randomly placed in gold colloids of varying sizes as the antenna. Therefore, bowtie nano-antennas can be used for single-molecule experiments in high concentration solutions. In a preliminary test, the enhanced signals were shown to arise from molecules near the bowtie which lingered near the gap for some time.

The two example fluorescent molecules selected for the demonstration are IR800cw carboxylate (Li-Cor) and indocyanine green (ICG) (Sigma-Aldrich). The absorption and emission spectra of the two dyes overlap well with the plasmon resonance from a 10 nm gap gold bowtie nano-antenna, so the bowtie would be expected to potentially enhance both the absorption and emission from both molecules when the molecules are located in or near the bowtie gap.

The maximum fluorescence enhancement (f) possible for a particular dye molecule coupled to the optimal gap region of the bowtie compared to an unenhanced single emitter is dependent upon the enhancement of the absorption of light ($f_E$) arising from locally enhanced pumping intensity as well as the enhancement or quenching of the fluorescence quantum efficiency ($f_\eta$) according to: $f = f_E f_\eta$.

The enhancement of the absorption of light is simply dependent upon the change in the local pump intensity ($|E|^2$) due to the bowtie's presence and has been previously calculated using Finite-Difference Time-Domain (FDTD) simulations to be a factor of 180 with 780 nm pumping for a molecule in the center of a 16 nm bowtie gap. The change in the quantum efficiency (QE), however, is highly dependent upon the intrinsic QE of the molecule according to:

$$f_\eta = \frac{\eta'}{\eta_0} = \frac{\frac{\gamma'_r}{\gamma_r}}{1 - \eta_0 + \eta_0\left(\frac{\gamma'_r}{\gamma_r} + \frac{\gamma'_{nr}}{\gamma_r}\right)}$$

where $\eta_0$ is the molecule's intrinsic QE, $\eta'$ is the molecule's QE when coupled to the bowtie, $\gamma_r$ is the molecule's intrinsic radiative rate, and $\gamma'_r$ and $\gamma'_{nr}$ are the molecule's radiative and non-radiative rates when coupled to the bowtie.

A suitable molecule for high-concentration FCS experiments is a molecule that has the highest fluorescence enhancement. The $\eta_0$ of ICG in water is 2.4%, which corresponds to a maximum fluorescence enhancement of 1,700 which occurs when a molecule is optimally located in the bowtie gap with absorption/emission dipole along the bowtie axis. The $\eta_0$ of ICG increases to 14% in ethanol, which corresponds to a much lower maximum fluorescence enhancement of 310, but this slightly larger value allows for this molecule/solvent combination to be measured in standard no-bowtie FCS measurements as a comparison. Finally, the $\eta_0$ of IR800cw in ethanol is 28%, which means it will have an even lower maximum fluorescence enhancement of 157.

Bowtie nano-antennas are fabricated on indium tin oxide coated glass substrates using E-beam lithography to have 70 nm sides, 20 nm thickness, and gaps near 20 nm. In order to immerse the bowties in concentrated solutions of dye molecules, a simple fluid cell is constructed from 2 coverslips, one with the fabricated bowtie nano-antennas on the surface and the other unstructured, and an o-ring sandwiched in between the coverslips. The coverslips and o-ring are first cleaned in water and then ozone-cleaned for 10 minutes, before adding the concentrated dye solutions.

Confocal fluorescence measurements of concentrated dye solutions on bowtie nano-antennas were performed using the specially designed confocal microscope with 780 nm continuous wave pumping (10 ms/pixel) shown in FIG. 4.

With a fluid containing molecules above the bowtie, at 1 µM concentration there are only 0.6 molecules/(100 nm)$^3$ region. Even with very few molecules present on average, it is easy to see fluorescence enhancement from bowties immersed in an IR800cw solution (100 nM concentration in ethanol) and in an ICG solution (1 µM concentration in water) as shown in FIG. 7. The enhancement is likely due to molecules that are stuck to the substrate surface instead of floating in solution, a conclusion supported by several pieces of experimental evidence. First, using separate observations of fluorescence from molecules in the presence of an ITO-coated surface without bowties, ICG was found to stick to the ITO surface in water, but not in ethanol (IR800cw sticks to the surface for either solvent). While bowties submerged in ICG in water easily showed enhanced fluorescence, when the solvent is changed to the solvent that suppresses sticking (ethanol), the enhancement is not observed because the time during which the molecule is near the bowtie gap is much smaller and the optical apparatus was not optimized for extremely short bursts of emission. Second, the concentration dependence suggests that the surface is nearly saturated with sticking molecules even at 100 nM concentration. This is evident from signal-to-background considerations; for example, bowties immersed in a highly concentrated solution of IR800cw (100 µM in ethanol) are only barely detectable above background. This implies that the gap region was already saturated with molecules on the surface at 100 nM concentration, so that by increasing the concentration by 1000 times, only the background would increase. When the optical intensity increases, the lingering time of molecules near the enhanced region appears to drop, but this is due to enhanced photobleaching.

Since the enhanced emission originates from molecules stuck to either the substrate or the gold in the bowtie gap, it is necessary to rule out Surface Enhanced Raman Scattering (SERS) from local hot spots with extreme chemical enhancements. It has been found that the Raman signal from molecules absorbed to small metal colloids can also be enhanced enough to be able to measure Raman scattering from single molecules. SERS, however, has a different spectral behavior as compared to fluorescence, so emission spectra were taken of the emission from both bulk and bowtie-enhanced molecules. The measured spectra show broad emission bands which are typical for room-temperature fluorescence measurements, and do not show any sharp features typically associated with Raman transitions (effectively ruling out SERS effects).

Time traces of the fluorescence emission intensity for single bowties immersed in a 1 solution of IR800cw in ethanol and ICG in water were observed as shown in FIG. 7. In both cases, bursts of fluorescence can be seen when a molecule enters the enhanced field region of the bowtie nano-antenna, and until the molecule eventually photobleaches. No single-molecule fluorescence flashing events are measured in the absence of the bowtie nano-antennas at 1 µM concentrations of either dye, as is expected since with large numbers of molecules contributing similar signals for the entire diffraction-limited illumination volume, the bursts are difficult to observe above the background (and the contrast in the autocorrelation disappears). The contrast between single enhanced molecules and background is much higher for ICG than for IR800cw. This difference supports the conclusion that ICG is a better molecule for bowtie FCS than IR800cw since it has a lower intrinsic QE and hence a higher bowtie-induced fluorescence enhancement.

In a fluorescence correlation spectroscopy (FCS) test, the fluorescence emission from a low concentration dye solution that can be irradiated by a focused laser beam was analyzed by calculating the autocorrelation of the emission signal. Artifacts are avoided from APD detector dead times by using a 50/50 beamsplitter and two detectors and extracting the autocorrelation according to:

$$G(\tau) = \frac{\langle \delta I_1(t) \delta I_2(t+\tau) \rangle}{\langle I_1(t) \rangle \langle I_2(t) \rangle}$$

where < > denotes the time average $I_i(t)$ is the fluorescence intensity on one of the two detectors at time t and the numerator utilizes deviations δ from the average value in the calculation. The fluctuations can arise from diffusion as molecules move in and out of the focal volume, or from internal dynamics of the emitter arising from triplet states, other dark states, or even the excited state lifetime.

To characterize the standard unenhanced FCS curves for the two molecules, ITO-coated coverslips were used to support 10 pM solutions of ICG and IR800cw in ethanol, and the FCS curves show typical diffusion fall-off and short-time dynamics below 10 µs from intermediate states, shown in FIGS. 8A-B 870 and FIGS. 9A-B 950. ICG had to be measured in ethanol because the QE was too low to measure in water without the assistance of the bowtie.

Figure 8:
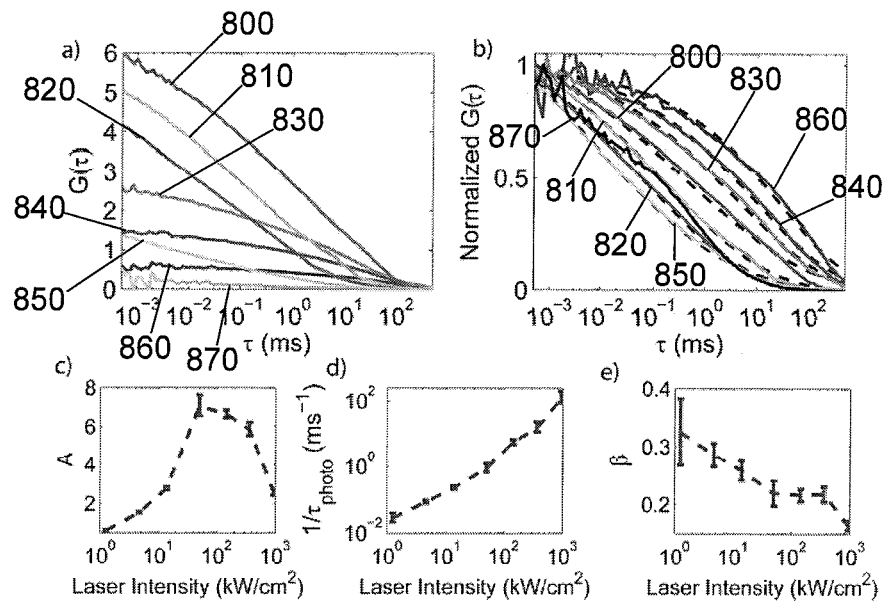
FIG. 8 shows FCS curves for a bowtie immersed in a solution of 1 µM ICG in water when illuminated with different intensities.

FIG. 8A shows FCS curves for a bowtie immersed in a solution of 1 µM ICG in water when illuminated with pump intensity 1.3 kW/cm² (860), 4.6 kW/cm² (840), 14 kW/cm² (830), 50 kW/cm² (800), 144 kW/cm² (810), 362 kW/cm² (820), and 940 kW/cm² (850). The 870 curve in FIG. 8A indicates the FCS curve for the same 1 µM ICG in water solution but without a bowtie nanoantenna at 110 kW/cm² laser intensity. FIG. 8B shows FCS curves from FIG. 8a normalized to their value at τ=100 ns and clearly show that the photobleaching time, $\tau_{photo}$, decreases as the laser intensity increases. The fits to each curve using the stretched exponential are plotted with dashed-lines. FIG. 8B also shows the FCS curve for a 10 pM solution of ICG in the absence of a bowtie nano-antenna with 2.9 MW/cm² laser intensity plotted in the 870 curve. FIGS. 8C-E show fit parameters used for fit curves shown in FIG. 8B using the stretched exponential function described herein.

Figure 9:
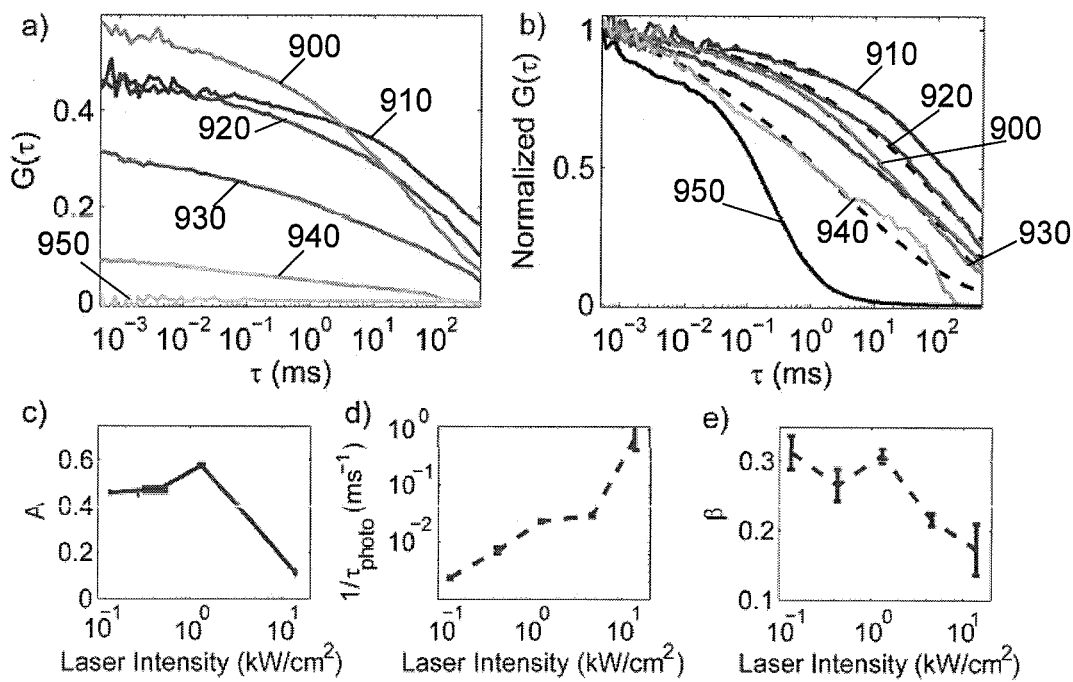
FIG. 9 shows FCS curves for a bowtie immersed in a solution of 100 nM IR800cw in ethanol when illuminated with different intensities.

FIG. 9A shows FCS curves for a bowtie immersed in a solution of 100 nM IR800cw in ethanol when illuminated with 0.14 kW/cm² (910), 0.47 kW/cm² (920), 1.3 kW/cm² (900), 4.6 kW/cm² (930), and 13.8 kW/cm² (940). The 950 curve of FIG. 9A indicates the FCS curve for the same 100 nM IR800 in ethanol solution but without a bowtie nano-antenna at 1.3 kW/cm² laser intensity. FIG. 9B shows FCS curves from FIG. 9A normalized to their value at τ=100 ns and clearly show that the photobleaching time decreases as the laser intensity increases (fits to each curve of using the stretched exponential are plotted with dashed-lines). FIG. 9B also shows the FCS curve for a 10 pM solution of IR800cw in the absence of a bowtie nano-antenna with 1.9 MW/cm² laser intensity plotted in the 950 curve; the usual falloff from simple diffusion is clearly present. FIGS. 9C-E show fit parameters used for fit curves shown in FIG. 9B.

At lower excitation intensities, for a single bowtie immersed in 1 µM ICG in water, the timescale for the bowtie FCS curve decay is much longer than the FCS curve in the absence of the bowtie nano-antenna, opposite the expected falloff in correlation due to diffusion. This difference in time scale is consistent with the picture that molecules transiently stick to the surface near the bowtie nanoantenna, and then photobleach. The simplest model for photobleaching is that a molecule has a fixed probability of photobleaching during any excitation cycle and this does not change with excitation intensity. In general, a molecule has a total number of photons that it tends to emit on average before photobleaching that remains constant for different excitation intensities. Rather, as the excitation intensity is increased, the molecule will emit the same total number of photons but in shorter periods of time, causing the photobleaching time, $\tau_{photo}$, to shorten. If there was a diffusion component to the FCS curve, it would not change with increasing power. This is not observed, therefore, the long-time decay in the bowtie FCS curves is not due to diffusion, but instead the long time decay reports on photobleaching times at different molecule positions and orientations on the surface.

Since an enhanced molecule can be in a number of different positions and orientations and still contribute to the correlation, then a continuum of different photobleaching times underlies the FCS curve. Photobleaching is often considered a Poisson process with exponential waiting time, but here a distribution of characteristic times should be present. The resulting multi-exponential behavior is commonly modeled with a stretched exponential. Therefore, the bowtie FCS curves were fit with the following equation:

$$G(\tau) = \frac{1}{N} e^{-(\tau/\tau_{photo})^\beta}.$$

where N scales with the concentration, $\tau_{photo}$ is the photobleaching time parameter, and β is the usual stretching parameter.

When β=1, the FCS curve is a single exponential, but as β decreases below 1 toward zero, the exponential is stretched more and more and is representative of the sum of more and more exponentials. As the excitation power increases, $(\tau_{photo})^{-1}$ increases, consistent with photobleaching behavior. For the bowtie FCS curves, β values between 0.15 and 0.32 are observed, indicating that the FCS curves are actually sums of a broad continuum of photobleaching times. Further, it is interesting to note that as the excitation intensity increases, β decreases, therefore, at higher excitation intensities there are more underlying exponentials than at lower excitation intensities. This is a reasonable observation given the fact that more and more non-optimally oriented and located molecules can contribute at higher intensity levels.

Turning now to the other fluorophore, IR800cw, the lower signal to background ratio makes the FCS curves have lower contrast and thus are more challenging to measure. As was measured for ICG bowtie FCS, the photobleaching time for IR800cw bowtie FCS is found to decrease as the excitation intensity increases.

Bowtie FCS and the use of bowties to enhance fluorescence bursts from weak emitters has been shown to be a useful alternative to zero-mode waveguides when studying molecules immobilized on the surface of a substrate at high (μM) concentrations. Bowtie FCS successfully measured the photobleaching (turn-off) times of high (1 μM) concentration of ICG in water as a function of laser intensity. In further embodiments, an enzyme could be attached to the surface near the bowtie and whenever it acts on a fluorescently labeled substrate molecule at μM concentrations, then due to the binding process, the fluorescent substrate molecule with its enhanced fluorescence will be held near the bowtie for an extended period of time, allowing for easy measurement. In a similar fashion, a biomolecule with a ligand binding site can be attached to the surface, and then fluorescently labeled ligands which bind to the biomolecule can be easily detected, and the unbinding times directly measured. With surface passivation to prevent sticking, the fluorescence bursts would be expected on a much shorter time scale corresponding only to diffusion through the volume or to the binding time to any surface-immobilized enzyme or target biomolecule.

For background and related technical information useful for implementing the above-disclosed embodiments, reference may be made to the published articles which correspond to the above-noted U.S. Provisional Application. See: Appendices A-B (Nature Photonics, Published Online 18 Oct. 2009 DOI: 10.1038/NPHOTON.2009.187), with Supplementary Supplementation; and Appendix C (Nature Photonics, Vol. 3, November 2009). Each of these publications and the entire set of appendices filed in the underlying provisional application are fully incorporated herein by reference in this regard.

While the present disclosure is amenable to various modifications and alternative forms, specifics thereof have been shown by way of example in the drawings and will be described in further detail. It should be understood that the intention is not to limit the disclosure to the particular embodiments and/or applications described. On the contrary, the intention is to cover all modifications, equivalents, and alternatives falling within the spirit and scope of the present disclosure.

What is claimed is:

1. An apparatus comprising:
a nano-antenna of at least two metallic end portions on a support structure;
the nano-antenna configured and arranged
with fluorescence-enhancing molecules fixed to a surface of the metallic end portions in a gap between the at least two metallic end portions whereat a fluid solution of fluorescent molecules can reside,
to receive and respond to optical energy by generating an electric field due to opposing charges via the at least two metallic end portions, each of the end portions being configured and arranged with a width that increases with distance away from the gap and therein concentrates the electric field within the gap, and
to use the opposing charges and the fluorescence-enhancing molecules to concentrate and enhance the electric field and fluorescence emission of the fluorescent molecules in the fluid solution when the fluid solution resides between the at least two metallic end portions; and
a photon-counting circuit configured and arranged to sense, due to the fluorescence of the fluorescent molecules, life-time or broadly peaking characteristics of spectral waveforms.

2. The apparatus of claim 1, wherein the gap is characterized by a dimension of less than 50 nm between the end portions, and the nano-antenna is a gold bowtie that is configured and arranged to enhance the fluorescence, of a single one of the fluorescent molecules centered in the gap between the end portions, by a factor of between 1000 and about 1340 relative to fluorescence of other ones of the fluorescent molecules in the gap.

3. The apparatus of claim 1, wherein each of the metallic end portions manifest characteristics of metal due to the metallic end portions being doped with metal ions, and the gap between the at least two metallic end portions is less than 50 nm.

4. The apparatus of claim 1, wherein the at least two metallic end portions include at least one of: gold, aluminum, silver, and copper, and the fluorescence-enhancing molecules are in the metallic end portions.

5. The apparatus of claim 1, wherein the fluorescent molecules are low-quantum efficiency-type molecules.

6. The apparatus of claim 1, wherein the fluorescent molecules are of a high concentration.

7. The apparatus of claim 1, wherein the photon-counting circuit senses the life-time characteristics of the spectral waveforms of the fluorescence emission.

8. The apparatus of claim 1, wherein the photon-counting circuit is configured and arranged to sense broadly peaking characteristics of the spectral waveforms.

9. The apparatus of claim 1, further including in or around the gap between the at least two metallic end portions, a fluid solution of fluorescent molecules, the fluorescent molecules being highly concentrated or a low-quantum efficiency-molecule type.

10. The apparatus of claim 9, wherein the photon-counting circuit senses the life-time characteristics of spectral waveforms of the fluorescent molecules.

11. The apparatus of claim 9, wherein the photon-counting circuit senses broadly peaking characteristics of the spectral waveforms.

12. The apparatus of claim 1, further including one or more of: a fluid solution of fluorescent molecules in or around the gap between the at least two metallic end portions, the fluorescent molecules being highly concentrated; a fluid solution of fluorescent molecules in or around the gap between the at least two metallic end portions, the fluorescent molecules being a low-quantum efficiency-molecule type; and further including a photon-counting circuit configured and arranged to sense spectral waveforms due to fluorescence of stimulated fluorescent molecules.

13. The apparatus of claim 1, further including a light emitting element configured and arranged to stimulate the fluorescent molecules, and wherein the at least two metallic end portions are doped with metallic ions of copper, gold, silver, or aluminum.

14. The apparatus of claim 1, further including a light emitting element configured and arranged to stimulate the fluorescent molecules, and wherein the fluorescent molecules are low-quantum efficiency-molecule type.

15. The apparatus of claim 1, further including a light emitting element configured and arranged to stimulate the fluorescent molecules, and wherein the fluorescent molecules are highly concentrated.

16. An apparatus comprising:
a bowtie nano-antenna of at least two metallic end portions on a support structure;
the bowtie nano-antenna configured and arranged
with fluorescence-enhancing molecules fixed to a surface of the metallic end portions in a gap of less than 50 nm between the at least two metallic end portions where a fluid solution of low-quantum efficiency-type fluorescent molecules reside,
to receive and respond to optical energy by generating an electric field due to opposing charges via the at least two metallic end portions, and
to enhance the electric field and fluorescence emission of the fluorescent molecules in the fluid solution when the fluid solution resides in the gap between the at least two metallic end portions.

17. The apparatus of claim 16, wherein the low-quantum efficiency-type molecules are highly concentrated, and wherein the metallic end portions are configured and arranged with a width that increases with distance away from the gap and therein concentrates the electric field in the gap.

18. An apparatus comprising:
a bowtie nano-antenna of at least two metallic end portions on a support structure; and
the bowtie nano-antenna configured and arranged
with fluorescence-enhancing molecules fixed to a surface of the metallic end portions and in a gap of less than 50 nm between the at least two metallic end portions where a fluid solution of highly concentrated fluorescent molecules reside,
to receive and respond to optical energy by generating an electric field due to opposing charges via the at least two metallic end portions, and
to enhance the electric field and fluorescence emission of the fluorescent molecules in the fluid solution when the fluid solution resides between the at least two metallic end portions.

19. The apparatus of claim 18, wherein the highly concentrated fluorescent molecules are low-quantum efficiency-type molecules, and wherein the metallic end portions are configured and arranged with a width that increases with distance away from the gap and therein concentrates the electric field into the gap.

20. A method of using an apparatus, comprising:
providing a fluid solution of low-quantum efficiency-type molecules in a gap between at least two metallic end portions of a nano-antenna, the nano-antenna having fluorescence-enhancing molecules fixed to a surface of the metallic end portions in the gap and being supported by a support structure, each of the metallic end portions having a width that increases with distance away from the gap;
generating an electric field due to opposing charges via the at least two metallic end portions in response to receiving optical energy;
enhancing the electric field and fluorescence emission of the low-quantum efficiency-type molecules in the fluid solution in response to receiving the optical energy, by using the increasing width of the metallic end portions to concentrate the electric field in the gap; and
sensing life-time or broadly peaking characteristics of spectral waveforms of the low-quantum efficiency-type molecules using a photon-counting circuit.

21. The method of claim 20, wherein the low-quantum efficiency-type molecules are highly concentrated, and providing a fluid solution of low-quantum efficiency-type molecules in a gap includes providing the fluid solution in a gap extending between the end portions and having a width of less than 50 nm.

22. The method of claim 20, wherein the life-time characteristics of the spectral waveforms are sensed by using the concentrated electric field to enhance the fluorescence of a single one of the fluorescent molecules centered in the gap between the end portions, relative to fluorescence of other ones of the fluorescent molecules in the gap.

23. The method of claim 20, wherein the broadly peaking characteristics of spectral waveforms are sensed.

24. A method of using an apparatus, comprising:
providing highly concentrated fluorescent molecules in a fluid solution in a gap of less than 50 nm between at least two metallic end portions of a nano-antenna, the nano-antenna configured and arranged with fluorescence-enhancing molecules fixed to a surface of the metallic end portions in the gap and being supported by a support structure;
generating an electric field due to opposing charges via the at least two metallic end portions in response to receiving optical energy;
enhancing the electric field and fluorescence emission of the highly concentrated fluorescent molecules in the fluid solution in response to receiving the optical energy; and
sensing life-time or broadly peaking characteristics of spectral waveforms of the highly concentrated fluorescent molecules using a photon-counting circuit.

25. The method of claim 24, wherein the highly concentrated fluorescent molecules are low-quantum efficiency-type molecules.

26. The method of claim 24, wherein the life-time characteristics of spectral waveforms are sensed.

27. The method of claim 24, wherein the broadly peaking characteristics of spectral waveforms are sensed.

28. An apparatus comprising:
a gold bowtie nano-antenna having at least two metallic end portions on a support structure;
the nano-antenna configured and arranged
with a gap between the at least two metallic end portions whereat a fluid solution of fluorescent molecules can reside,
to receive and respond to optical energy by generating an electric field due to opposing charges via the at least two metallic end portions, each of the end portions being configured and arranged with a width that increases with distance away from the gap and therein concentrates the electric field within the gap, and
to use the opposing charges to concentrate and enhance the electric field and fluorescence emission of the fluorescent molecules in the fluid solution when the fluid solution resides between the at least two metallic end portions, wherein the gold bowtie nano-antenna is configured and arranged to enhance the fluorescence, of a single one of the fluorescent molecules centered in the gap between the end portions, by a factor of between 1000 and about 1340 relative to fluorescence of other ones of the fluorescent molecules in the gap; and a photon-counting circuit configured and arranged to sense, due to the fluorescence of the fluorescent molecules, life-time or broadly peaking characteristics of spectral waveforms.

29. The apparatus of claim 28, wherein the nano-antenna includes fluorescence-enhancing molecules over the metallic end portions, the fluorescence-enhancing molecules being selected to enhance a type of fluorescent molecules including the single one of the fluorescent molecules.

30. The apparatus of claim 28, wherein the nano-antenna includes fluorescence-enhancing molecules over the metallic end portions.

31. The apparatus of claim 28, wherein the nano-antenna includes fluorescence-enhancing molecules in the metallic end portions.

* * * * *